(12) United States Patent
Schweizer et al.

(10) Patent No.: US 8,557,322 B2
(45) Date of Patent: Oct. 15, 2013

(54) PREPARATION OF CANOLA PROTEIN ISOLATE AND USE IN AQUACULTURE

(75) Inventors: Martin Schweizer, Winnipeg (CA); Brent E. Green, Warren (CA); Randy Willardsen, Roseville, CA (US)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 1077 days.

(21) Appl. No.: 10/589,761

(22) PCT Filed: Feb. 17, 2005

(86) PCT No.: PCT/CA2005/000201
§ 371 (c)(1), (2), (4) Date: Oct. 17, 2007

(87) PCT Pub. No.: WO2005/077201
PCT Pub. Date: Aug. 25, 2005

(65) Prior Publication Data
US 2008/0166469 A1    Jul. 10, 2008

Related U.S. Application Data

(60) Provisional application No. 60/544,346, filed on Feb. 17, 2004.

(51) Int. Cl.
*A23J 1/18* (2006.01)

(52) U.S. Cl.
USPC .......................................... 426/656; 426/805

(58) Field of Classification Search
USPC ................................. 426/656, 805
See application file for complete search history.

(56) References Cited

U.S. PATENT DOCUMENTS

| | | | | |
|---|---|---|---|---|
| 6,005,076 | A * | 12/1999 | Murray | 530/377 |
| 6,800,308 | B2 * | 10/2004 | Maenz et al. | 426/44 |
| 6,955,831 | B2 * | 10/2005 | Higgs et al. | 426/630 |
| 2003/0170376 | A1 * | 9/2003 | Hiron et al. | 426/656 |

FOREIGN PATENT DOCUMENTS

| | | |
|---|---|---|
| CA | 2335745 | 8/2002 |
| JP | 10229828 A * | 9/1998 |
| WO | WO 02/089597 | 11/2002 |
| WO | WO 03/043439 | 5/2003 |
| WO | WO 03/053157 | 7/2003 |
| WO | WO 03/088760 | 10/2003 |
| WO | WO 03088760 A1 * | 10/2003 |
| WO | WO 04/000031 | 12/2003 |

OTHER PUBLICATIONS

Klockeman et al. J. Agric. Food Chem., 1997, 45, pp. 3867-3870.*
Mwachireya et al. Aquaculture Nutrition, vol. 5, Issue 2, pp. 73-82, Jun. 1999.*
Ismond et al. Food Chemsitry, 1992, vol. 45(2), pp. 125-127, abstract only.*
Gillberg et al. Preparation of rapeseed protein isolates JFood Sci., vol. 41, pp. 1070-1075, 1976.*
Forster et al. Aquaculture, 1999, vol. 179, pp. 109-125.*
Higgs et al. "Nutrition and Utilization Technology in Aquaculture". Eds Lim et al., AOCS Press, Chapter 11, pp. 130, 143, Published 1995.*
Higgs et al. "Canola Protein offers hope for efficient salmon production", International Congress on the biol. of Fish, downloaded from http://replay.waybackmachine.org/20040217190907/http://www.pac.dfo-mpo.gc.ca/congress, dated Feb. 17, 2004.*
"Future in food for canola protein ingredient" (Breaking News on Food and Beverage Development-Europe, downloaded from http://www.foodnavigator.com/Science-Nutrition/Future-in-food-for-canola-protein-ingredient, dated Apr. 10, 2002.*
Zijlstra et al. "Ingredient Fractionation: The value of value-added processing for Animal Nutrition" downloaded from http://www.prairieswine.com/ingredient-fractionation-the-value-of-value-added-processing-for-animal-nutrition dated Jan. 1, 2004, 12 pages.*

* cited by examiner

*Primary Examiner* — Chhaya Sayala
(74) *Attorney, Agent, or Firm* — Michael I. Stewart; Sim & McBurney

(57) ABSTRACT

A canola protein isolate useful in aquaculture is formed by a procedure in which canola oil seed meal is extracted to cause solubilization of protein in the canola oil seed meal to form an aqueous protein solution having a protein content of about 5 to about 40 g/L and a pH of about 5 to about 6.8. After separation of the aqueous protein solution from the residual canola oil seed meal, the protein concentration is increased to at least about 50 g/L while maintaining the ionic strength substantially constant by using a selective membrane technique. The concentrated protein solution is dried to provide a canola protein isolate having a protein content of at least about 90 wt % (N×6.25) d.b.

2 Claims, 2 Drawing Sheets

FIGURE 1: Bench Study HPLC-SEC Chromatograms
Bench Extract December 11, 2003: SEC-HPLC chromatogram 1:4 dil. 50-uL injection.
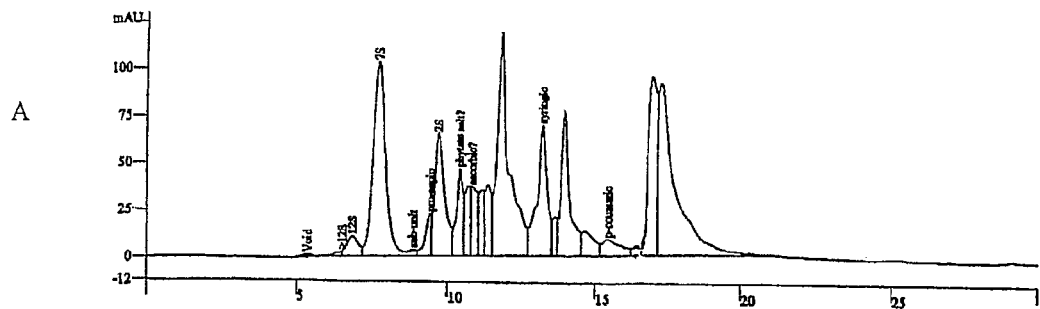
A
Bench DF Permeate December 12, 2003: SEC-HPLC chromatogram no dil. 50-uL injection.
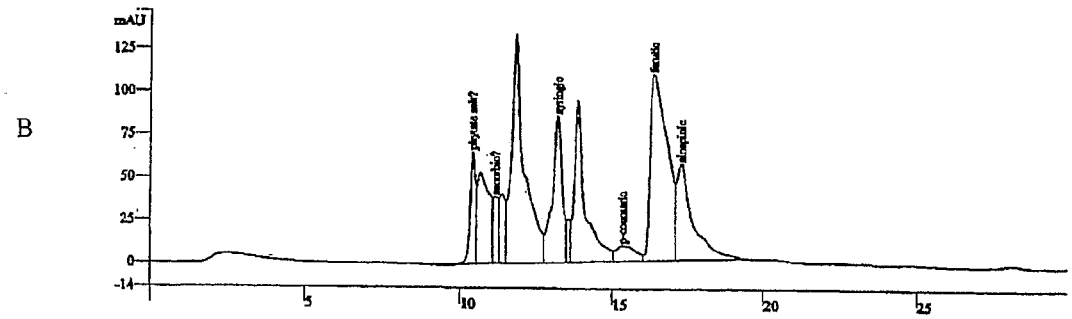
B
Bench DF UF Dialyzed Isolate December 17, 2003: SEC-HPLC chromatogram 1% 50-uL injection.
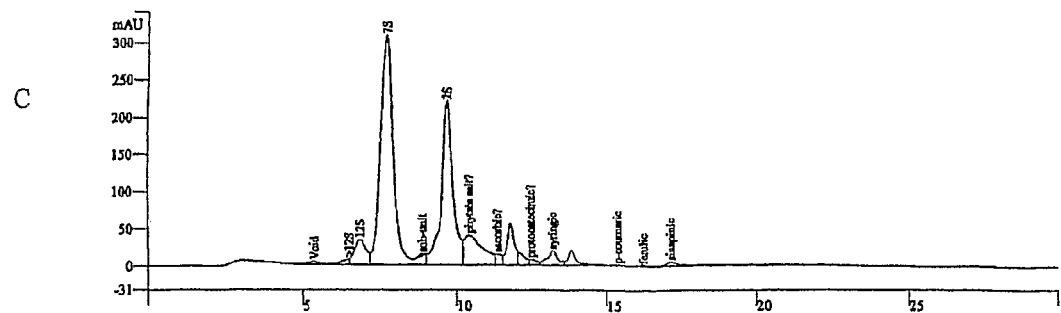
C FIGURE 2: BW-AL022-I02-03A #1 C500 HPLC-SEC Chromatograms
I02 Isolate September 19, 2003: SEC-HPLC chromatogram 1% 50-uL injection
A
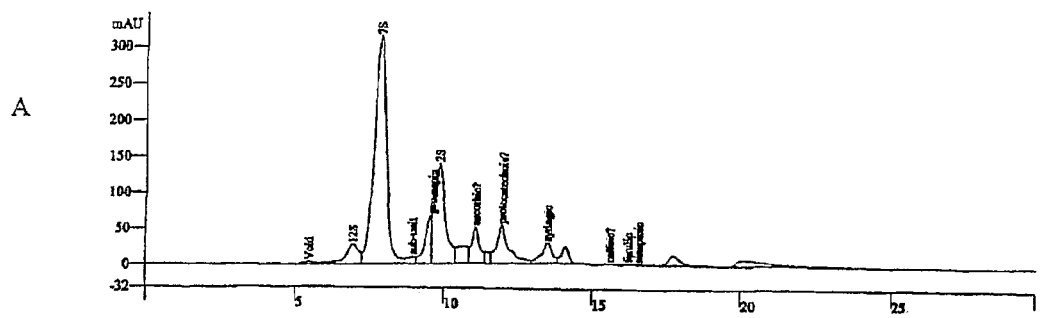
I02 Isolate December 18, 2003: SEC-HPLC chromatogram 1% 50-uL injection
B
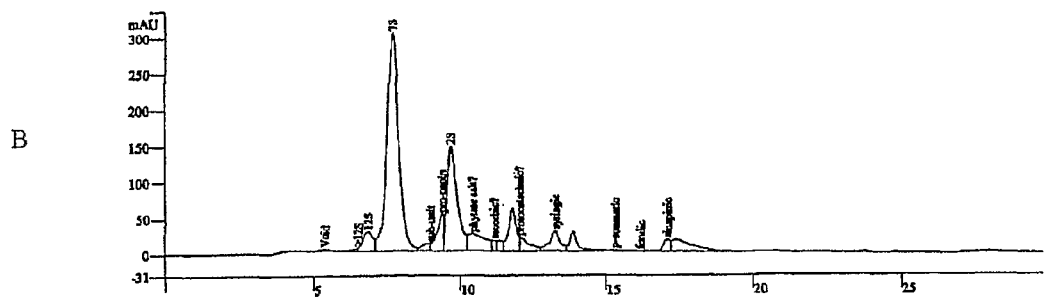
All samples prepared with 0.10M NaCl.

PREPARATION OF CANOLA PROTEIN ISOLATE AND USE IN AQUACULTURE

REFERENCE TO RELATED APPLICATION

This application claims priority pursuant to 35 USC 119(e) from U.S. Provisional Patent Application No. 60/544,346 filed Feb. 17, 2004.

FIELD OF INVENTION

The present invention relates to the preparation of canola protein isolates and their use in aquaculture.

BACKGROUND TO THE INVENTION

Canola protein isolates can be formed from canola oil seed meal. In copending U.S. patent application Ser. No. 10/137,391 filed May 3, 2002 and corresponding PCT Publication No. WO 02/089597, assigned to the assignee hereof and the disclosures of which are incorporated herein by reference, there is described a method of making canola protein isolates from canola oil seed meal, such isolates having at least 100 wt % protein content N×6.25). The procedure involves a multiple step process comprising extracting canola oil seed meal using a salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous gluten-like protein micellar mass (PMM), and recovering the protein micellar mass from supernatant having a protein content of at least about 100 wt % as determined by Kjeldahl nitrogen (N×6.25). As used herein, protein content is determined on a dry weight basis. The recovered PMM may be dried.

In one embodiment of the process described above and as specifically described in application Ser. No. 10/137,391, the supernatant from the PMM settling step is processed to recover a protein isolate comprising dried protein from the wet PMM and supernatant. This procedure may be effected by initially concentrating the supernatant using ultrafiltration membranes, mixing the concentrated supernatant with the wet PMM and drying the mixture. The resulting canola protein isolate has a high purity of at least about 90 wt % of protein (N×6.25), preferably at least about 100 wt % protein (N×6.25).

In another embodiment of the process described above and as specifically described in application Ser. No. 10/137,391, the supernatant from the PMM settling step is processed to recover a protein from the supernatant. This procedure may be effected by initially concentrating the supernatant using ultrafiltration membranes and drying the concentrate. The resulting canola protein isolate has a high purity of at least about 90 wt % protein (N×6.25), preferably at least about 100 wt % protein (N×6.25).

The procedures described in the aforementioned US patent applications are essentially batch procedures. In copending U.S. patent application Ser. No. 10/298,678 filed Nov. 19, 2002 and corresponding PCT Publication No. WO 03/043439, assigned to the assignee hereof and the disclosures of which are incorporated herein by reference, there is described a continuous process for making canola protein isolates. In accordance therewith, canola oil seed meal is continuously mixed with a salt solution, the mixture is conveyed through a pipe while extracting protein from the canola oil seed meal to form an aqueous protein solution, the aqueous protein solution is continuously separated from residual canola oil seed meal, the aqueous protein solution is continuously conveyed through a selective membrane operation to increase the protein content of the aqueous protein solution to at least about 200 g/L while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is removed from the settling vessel and may be dried. The PMM has a protein content of at least about 90 wt % as determined by Kjeldahl nitrogen (N×6.25), preferably at least about 100 wt % (N×6.25).

As described in the aforementioned U.S. patent application Ser. No. 10/137,391, the overflowed supernatant may be processed to recover canola protein isolate therefrom.

Canola seed is known to contain about 10 to about 30 wt % proteins and several different protein components have been identified. These proteins are distinguished by different sedimentation coefficients (S). These known and identified proteins include a 12 S globulin, known as cruciferin, and a 2 S storage protein, known as napin.

As described in copending U.S. patent application Ser. No. 10/413,371 filed Apr. 15, 2003 and corresponding PCT Publication No. WO 03/088760, assigned to the assignee hereof and the disclosures of which are incorporated herein by references, the PMM-derived canola protein isolate consists predominantly of a 7 S protein along with some 12 S protein while the supernatant-derived canola protein isolate consists predominantly of the 2 S protein.

In such prior process, canola protein isolates are separately derived from the concentrated canola protein solution by precipitating PMM and separately processing the supernatant to obtain additional quantities of canola protein solution.

Canola is also known as rapeseed or oil seed rape.

SUMMARY OF INVENTION

In the present invention, the concentrated protein solution resulting from the protein concentration step is dried directly without processing to produce PMM and separately processing the supernatant. This procedure simplifies the production of a canola protein isolate which has a broad spectrum of 12 S, 7 S and 2 S proteins. Because of the lesser number of process steps, the isolate is formed in a more economic manner.

Accordingly, in one aspect of the present invention, there is provided a process of preparing a canola protein isolate, which comprises (a) extracting a canola oil seed meal to cause solubilization of protein in said canola oil seed meal and to form an aqueous protein solution having a protein content of about 5 to about 40 g/L and a pH of about 5 to about 6.8; (b) separating the aqueous protein solution from the residual canola oil seed meal, (c) increasing the protein concentration of said aqueous protein solution to at least about 50 g/L while maintaining the ionic strength substantially constant by using a selective membrane technique to provide a concentrated protein solution; and (d) drying the concentrated protein solution to provide a canola protein isolate having a protein content of at least about 90 wt % (N×6.25) on a dry weight basis.

The canola protein isolate produced in accordance with the present invention has a canola protein profile of about 25 to about 55 wt % of 2 S canola protein, about 45 to about 75 wt % of 7 S canola protein and about 0 to about 15 wt % of 12 S canola protein, preferably about 40 to about 50 wt % of 2 S canola protein, about 50 to about 60 wt % of 7 S canola protein and about 1 to about 5 wt % of 12 S canola protein.

The canola protein isolate produced according to the process herein may be used in conventional applications of protein isolates, such as, protein fortification of processed foods, emulsification of oils, body formers in baked goods and foaming agents in products which entrap gases. In addition, the canola protein isolates may be formed into protein fibers, useful in meat analogs, may be used as an egg white substitute or extender in food products where egg white is used as a binder. The canola protein isolate may be used as nutritional supplements. Other uses of the canola protein isolate are in pet foods, animal feed, aquaculture and in industrial and cosmetic applications and in personal care products.

Since the protein isolates which are formed by the process of the present invention are generally of lesser purity, in particular, a higher salt content, than obtained by the procedures described in the aforementioned US patent applications, they are preferably used in non-human applications. One particular use of the protein isolates is as a feed in aquaculture, as described in more detail below. However, the protein isolates may be processed to reduce the residual salt content by any convenient procedure, such as by dialysis or diafiltration.

According to another aspect of the present invention, there is provided a feed composition for aquaculture comprising a canola protein isolate produced by the method provided herein. The feed composition may be especially formulated for feeding salmonids, including salmon and trout.

BRIEF DESCRIPTION OF DRAWINGS

FIGS. 1A to 1C are HPLC chromatograms profiles of samples from a bench extraction procedure to produce canola protein isolate; and FIGS. 2A and 2B are HPLC chromatograms profiles of a canola protein isolate proceeded in a pilot plant scale extraction procedure.

GENERAL DESCRIPTION OF INVENTION

The canola protein isolate may be isolated from canola oil seed meal by either a batch process or a continuous process or a semi-continuous process as generally described in the aforementioned United States patent applications.

The initial step of the process of providing the canola protein isolates involves solubilizing proteinaceous material from canola oil seed meal. The proteinaceous material recovered from canola seed meal may be the protein naturally occurring in canola seed or other oil seeds or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, such as in aquaculture, non-food-grade chemicals may be used. The salt usually is sodium chloride, although other salts, such as, potassium chloride, may be used. The salt solution has an ionic strength of at least about 0.05, preferably at least about 0.10, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

It is usually preferred to utilize an ionic strength value less than about 0.8, and more preferably a value of about 0.1 to about 0.6.

In a batch process, the salt solubilization of the protein is effected at a temperature of at least about 5° C. and preferably up to about 35° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 35° C. is chosen since the process becomes uneconomic at higher temperature levels in a batch mode.

In a continuous process, the extraction of the protein from the canola oil seed meal is carried out in any manner consistent with effecting a continuous extraction of protein from the canola oil seed meal. In one embodiment, the canola oil seed meal is continuously mixed with a food grade salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure preferably is effect at elevated temperatures, preferably above about 35° C., generally up to about 65° C.

The aqueous food grade salt solution and the canola oil seed meal have a natural pH of about 5 to about 6.8. pH values of about 5.3 to about 6.2 are preferred.

The pH of the salt solution may be adjusted to any desired value within the range of about 5 to about 6.8 for use in the extraction step by the use of any convenient acid, usually hydrochloric acid, or alkali, usually sodium hydroxide, as required.

The concentration of oil seed meal in the food grade salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous salt solution may contain an antioxidant. The antioxidant may be any convenient antioxidant, such as sodium sulfite or ascorbic acid. The quantity of antioxidant employed may vary from about 0.01 to about 1 wt %, preferably about 0.05 wt %. The antioxidant serves to inhibit oxidation of phenolics in the protein solution.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee hereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, may be added to the protein solution after separation from the residual oil seed meal in order to maintain the protein in solution during the concentration step described below. When a colour removal step and/or a first fat removal step is carried out, the salt generally is added after completion of such operations.

Another alternative procedure is to extract the oil seed meal with the food grade salt solution at a relatively high pH value above about 6.8, generally up to about 9.9. The pH of the food grade salt solution, may be adjusted in pH to the desired alkaline value by the use of any convenient food-grade alkali, such as aqueous sodium hydroxide solution. Alternatively, the oil seed meal may be extracted with the salt solution at a relatively low pH below about pH 5, generally down to about pH 3. Where such alternative is employed, the aqueous phase resulting from the oil seed meal extraction step then is separated from the residual canola meal, in any convenient manner, such as by employing a decanter centrifuge, followed by disc centrifugation and/or filtration to remove residual meal. The separated residual meal may be dried for disposal.

The aqueous protein solution resulting from the high or low pH extraction step then is pH adjusted to the range of about 5 to about 6.8, preferably about 5.3 to about 6.2, as discussed above, prior to further processing as discussed below. Such pH adjustment may be effected using any convenient acid, such as hydrochloric acid, or alkali, such as sodium hydroxide, as appropriate.

The aqueous protein solution then is concentrated, usually about 4 to about 20 fold, to increase the protein concentration thereof while maintaining the ionic strength thereof substantially constant. Such concentration generally is effected to provide a concentrated protein solution having a protein concentration of at least about 50 g/L, preferably at least about 200 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off (MWCO), such as about 3000 to about 100,000 daltons, preferably about 5000 to about 10,000 daltons, having regard to differing membrane materials and configurations. The membranes may be hollow-fibre or spiral-wound. For continuous operation, the membranes may be dimensioned to permit the desired degree of concentration as the aqueous protein solution passes through the membranes.

The concentrated protein solution then may be subjected to a diafiltration step using an aqueous salt solution of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of contamination are removed from the aqueous protein solution by passage through the membrane with the permeate. The diafiltration operation may be effected until no significant further quantities of phenolics and visible colour are present in the permeate. Such diafiltration may be effected using a membrane having a molecular weight cut-off in the range of about 3000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and the diafiltration step may be effected at any convenient temperature, generally about 20° to about 60° C., and for the period of time to effect the desired degree of concentration. The temperature and other conditions used to some degree depend upon the membrane equipment used to effect the concentration and the desired protein concentration of the solution.

The concentrating of the protein solution to the preferred concentration above about 200 g/L in this step not only increases the process yield to levels above about 40% in terms of the proportion of extracted protein which is recovered as dried protein isolate, preferably above about 80%, but also decreases the salt concentration of the final protein isolate after drying. The ability to control the salt concentration of the isolate is important in applications of the isolate where variations in salt concentrations affect the functional and sensory properties in a specific food application.

As is well known, ultrafiltration and similar selective membrane techniques permit low molecular weight species to pass therethrough while preventing higher molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

The concentrated and optionally diafiltered protein solution may be subject to a further defatting operation, if required, as described in U.S. Pat. Nos. 5,844,086 and 6,005,076.

The concentrated and optionally diafiltered protein solution may be subject to a colour removal operation as an alternative to the colour removal operation described above. Powdered activated carbon may be used herein as well as granulated activated carbon (GAC). Another material which may be used as a colour adsorbing agent is polyvinyl pyrrolidone.

The colour absorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour adsorbing agent, an amount of about 0.5 to about 5 w/v, preferably about 2 to about 3% w/v, may be used. The colour adsorbing agent may be removed from the canola protein solution by any convenient means, such as by filtration.

The concentrated and optionally diafiltered protein solution resulting from the optional colour removal step may be subjected to pasteurization to kill any bacteria which may have been present in the original meal as a result of storage or otherwise and extracted from the meal into the canola protein isolate solution in the extraction step. Such pasteurization may be effected under any desired pasteurization conditions. Generally, the concentrated and optionally diafiltered protein solution is heated to a temperature of about 55° to about 70° C., preferably about 60° to about 65° C., for about 10 to about 15 minutes, preferably about 10 minutes. The pasteurized concentrated protein solution then may be cooled for further processing as described below, preferably to a temperature of about 25° to about 40° C.

The concentrated protein solution resulting from the concentration step, optional diafiltration step, optional colour removal step and optional defatting step then is dried by any convenient technique, such as spray drying or freeze drying, to a dry form to provide a canola protein isolate having a protein content of at least about 90 wt % protein (N×6.25), preferably at least about 100 wt % protein (N×6.25), and is substantially undenatured (as determined by differential scanning calorimetry). The canola protein isolate has a canola protein profile of about 25 to about 55 wt % of 2 S canola protein, about 45 to about 75 wt % of 7 S canola protein and about 0 to about 15 wt % of 12 S canola protein, preferably about 40 to about 50 wt % of 2 S canola protein, about 50 to about 60 wt % of 7 S canola protein and about 1 to about 5 wt % of 12 S canola protein As mentioned previously, one potential use of the canola protein isolate is in aquaculture. In farmed salmonid production, feed accounts for about 35 to 60% of the operating expenses and about half of the cost of feed stems from protein sources. Premium quality fish meals are used as the predominant source of protein in diets for salmonids because they are highly palatable and have high levels of digestable protein and energy and excellent amino acid and fatty acid profiles.

However, fish meals vary in quality, availability and price. Quality is affected by type and freshness of raw material and processing and storage conditions, as well as the ratio of soluble materials to presscake and the level of antioxidants.

It is predicted that the cost of fish meal will increase because of increased demands for finfish and crustacean culture, pet foods and specialty livestock feeds. Since the profitability of aquaculture depends on the relationship between the production cost and the market value of the farmed product, higher fish meal prices will mean increased costs of production and hence reduced margins for profit.

One way of reducing the production cost is through the development of new cheaper protein products to partially or wholly replace fish meal in salmonid diets. One source of a substitute for fish meal is oil seed meals, including canola oil seed meal. Such meals have fairly constant chemical composition and the cost of the meals is less than half that of high quality fish meals on a per kilogram protein basis. In addition, canola oil seed meal has an excellent rating based on the essential amino acid profile required by fish, as set forth in Table 6 below.

However, there are drawbacks to the use of canola oil seed meal owing to the presence of anti-nutritional factors (ANF), including phytic acid, glucosinolates, and phenolic compounds and insoluble fibre, which reduce the palatability and digestibility of the meal.

An unpublished study assessed the nutrition value of a canola protein concentrate (74 wt % protein) for rainbow trout (*Oncorhynchus mykiss*) in freshwater and Atlantic salmon (*Salmo salar*) in seawater.

In terms of protein digestibility, the canola protein product had a protein digestibility coefficient better than fish meal, an energy digestibility coefficient similar to fish meal and a calculated digestible energy similar to fish meal. The canola protein product, even at lower than optimum protein concentrations, showed the same growth ratio and feed intake as a commercial feed material.

The protein efficiency ratio (PER) is the single most important positive indicator for all the protein preparations. The canola protein product used in the unpublished study had less than optimal protein concentrations resulting from processing difficulties but, nevertheless the canola protein product diet had a comparable PER to a basal diet which was a special research diet and a special commercial diet. The PER of the special commercial diet was statistically the same as the canola protein product and basal PER values. These results are not achievable with soy protein, either in the form of a concentrate or isolate.

Having regard to the protein distribution in the product of the invention and the provision of a true protein isolate by the procedure described herein, it is expected that improved feeding results, compared to those achieved in the unpublished study, can be achieved for Salmonids by using the product of the invention.

When the canola protein isolate is formed by drying of the concentrated protein solution, the product contains a significantly greater concentration of residual salt than isolation via the PMM procedure discussed in the aforementioned prior art U.S. patent application Ser. No. 10/137,391. The presence of the salt is not detrimental to certain uses of the protein isolate, for example, in the use in aquaculture.

However, where the presence of the salt is detrimental to the intended use of the canola protein isolate, salt may be removed by dialyzing or diafiltering an aqueous solution of the protein, which may be in the form of the concentrated, optionally diafiltered, canola protein solution, prior to drying.

EXAMPLES

Example 1

This Example illustrates the procedure of the invention for the provision of canola protein isolates.

150 kg of commercial canola oil seed meal lot AL022 was added to 1010.5 L 0.1M saline (NaCl) at 19.8° C. and mixed for 30 minutes to provide an aqueous protein solution. At the halfway point of mixing (15 minutes), 0.05 wt % or 500 g w/v of ascorbic acid was added as an antioxidant. The extraction pH was 6.12 with no adjustment being made to the natural pH of the saline.

In order to remove the meal from the extracted solution, meal slurry was passed over a vacuum filter belt and a solution of 790 L with an average protein content of 1.74 wt % (17.4 g/L) was the result.

This solution was then passed through a desludger centrifuge and filter press housing 2.0 um pads in order to further clarify the protein solution. The final clarified protein extract had a volume of 780 L and a protein content of 1.58 wt % (15.8 g/L).

A 700 L aliquot of the clarified protein solution was then ultrafiltered (UF) on a 2-membrane system using polyvinyldiene difluoride (PVDF) 5 spiral wound membranes. These membranes have a MWCO range of 5000 Daltons. Total volume reduction was from 700 L down to 32 L or 21.8 times volume reduction. The resulting 32 L of concentrated protein solution or retentate had an average protein content of 25.10 wt % (251 g/L).

The retentate from the UF step was pasteurized at 60° C. for 10 minutes and aliquots were then dried on an APV spray dryer.

Final protein content of the dried product was 93.08 wt % as is and on dry weight basis 95.46 wt % (N×6.25). (Percentage nitrogen values were determined using a Leco FP528 Nitrogen Determinator). The batch was designated BW-AL022-I02-03A.

Example 2

This Example describes the preparation of a laboratory scale sample of canola protein isolate.

75 g of the same canola meal as used in Example 1 was added to 500 mL of 0.10 M saline solution (15% w/w) and the mixture was shaken for 30 minutes at 220 rpm on a rotational shaker. The extract, containing 1.99 wt % protein, was centrifuged for 20 minutes at 10,000 rpm and filtered through crepe-fluted filter paper.

350 ml of filtrate was concentrated on an Amicon Ultrafiltration unit using a 5,000 MWCO polyethersulfone (PES) membrane until 150 ml of retentate was collected. The retentate was diafiltered (DF) with 350 L of 0.1 M saline solution to produce 75 ml of DF retentate containing 6.24 wt % protein.

The retentate was dialyzed using Spectra/Por 6 to 8,000 MWCO tubing at refrigerated temperature. The dialyzed sample was frozen and then freeze-dried. The resulting canola protein isolate had a protein content of 101 wt % (N×6.25).

Example 3

This Example provides protein analysis of the canola protein isolates produced in Examples 1 and 2.

HPLC analysis was conducted on the canola protein isolates prepared as described in Examples 1 and 2. HPLC chromatograms of the bench extract, bench DF permeate and the bench DF UF dialyzed canola protein isolate are shown in FIGS. 1A, 1B and 1C, respectively.

HPLC chromatograms of the BW-AL022-I02-03A samples on two different dates are shown in FIGS. 2A and 2B.

Analysis of the canola protein isolates prepared as described in Examples 1 and 2 is contained in Tables 1 to 5 below. Table 5 contains amino acid analysis of the samples in comparison to typical PMM-derived (C300) and supernatant derived (C200) canola protein isolates, prepared as described in copending U.S. patent application Ser. No. 10/266,701 filed Oct. 9, 2002, assigned to the assignee hereof and the disclosure of which is incorporated herein by reference.

As may be seen from this data, the bench isolate (Example 2) shows a higher protein ratio than the I02 isolate (Example 1), based on peak areas. Both indicate that the globular proteins (7 S, 12 S, >12 S, and sub-unit) comprise about ⅔rd of the total protein peak areas, with the albumins (2 S and pronapin) contributing the other ⅓rd.

Other components found in the HPLC chromatograms indicate a relatively higher phytate level in the bench isolate, with a lower phenolic (and miscellaneous) content, based on peak areas. This result indicated that the bench isolate contained less free phenolic acid content than the I02 isolate. Colour differences, based on $A_{330}$, may be due to bound phenolics on the protein, which are not removable on the filter membranes.

The I02 HPLC-SEC (FIG. 2, Table 2) profile remained largely unchanged from the initial scan made on Sep. 19, 2003, to the more current run on Dec. 18, 2003, with the exception of ascorbic acid. Ascorbic acid oxidizes over time and was reduced in quantity, as determined by peak area, over this time frame. As a result, the other components increased in ratio, as shown, but this had little effect on the protein ratios.

The HPLC-SEC analyses of the bench samples, (Extract, UF Permeate, DF Permeate, DF Retentate and DF dialyzed FD Retentate resolubilized) (FIG. 1, Table 1), indicates that UF, DF and dialysis steps removed the majority of the phenolics and miscellaneous components, but was less effective with phytic acid removal. Phytic acid tends to have a strong association with protein. Even so, phytic acid was observed in the bench permeate HPLC chromatograms, which indicates partial removal through the membranes, (perhaps 20 to 30% of the total).

The Example 1 isolate contained salt and other minerals as shown, amounting to about 3% of the final dry weight of isolate (Table 3). No toxic elements were detected. The results show that the bench isolate is higher in protein, due to the DF and dialysis steps used in the preparation of this sample.

The amino acid analysis results were converted to "grams per 100 grams amino acids" in Tables 4A and 4B. The averages and standard deviations are also shown and indicate minimal differences. This is expected since the DF and dialysis steps remove non-proteins, which would not affect the amino acid balance in any significant way unless there were a lot of free amino acids and peptides.

Table 5 compares the current sample amino acid profiles with results from earlier studies. The current retentates are very similar in composition to the earlier retentates (from A8 and A10 meals) as well as a Puratein sample from A10 meal. Puratein is a mixture of PMM and Supertein and should be similar to the retentate analysis.

Table 5 also shows C200 and C300 (A10 meal) amino acid profiles. The retentate and Puratein samples fall between these two isolates, which would be expected.

Lysine is an essential amino acid that is in low abundance for cereals. Oilseeds, particularly canola, tend to have higher levels of lysine. The retentate analysis reveals a significant amount of lysine and this would improve the nutritional quality of this isolate, (even for fish or other non-human feed). The essential amino acid composition is quite high for retentate isolate, as is shown at the bottom of Table 5.

Overall, analysis shows that retentate, C500, is an isolate with a quality amino acid composition that ranges between C200 and C300. This isolate has low levels of non-proteins, and the bench study shows that salts, phenolics and other unknown substances are removed by ultra-filtration. Diafiltration and dialysis can improve this elimination of non-proteins, as shown by the bench extraction data. However, this is not required to produce an isolate, as is shown by the I02 results.

SUMMARY OF DISCLOSURE

In summary of the disclosure, there is provided a novel process for the preparation of canola oil seed protein isolates having multiple uses, including in aquaculture. Modifications are possible within the scope of the invention.

TABLE 1

C500 Sample, UF DF FD, Lab #21,681, Dec. 17-19, 2003

| Variable: | Average | Std. Dev. |
|---|---|---|
| Moisture | n.d. | n.d. |
| Leco protein (as is) | 101.09% | 0.03% |
| Leco protein (dry basis) | n.d. | n.d. |

C500 Sample, Lab #21,681, HPLC-SEC Results

| Variable: | Extract Lab #21670 Dil. 1:4 | Permeate Lab# 21,679 neat | DF Permeate Lab #21,680 neat | DF Retentate Lab #21,681 Dil. 1:4 | DF retentate FD, lab #21681 1% W/V |
|---|---|---|---|---|---|
| Protein % of Total Area | 23.8% | 0.0% | 0.0% | 62.6% | 77.3% |
| Phytate % of Total Area | 3.3% | 5.2% | 4.3% | 11.2% | 8.7% |
| Phenolics % of Total Area | 37.6% | 52.2% | 47.6% | 12.7% | 3.6% |
| Misc. % of Total Area | 35.3% | 42.6% | 48.1% | 13.5% | 10.4% |
| >12S + 12S % of protein Area | 6.5% | 0.0% | 0.0% | 6.9% | 6.7% |
| 7S % of protein Area | 58.0% | 0.0% | 0.0% | 57.2% | 57.7% |
| 7S Sub-unit % of protein Area | 0.2% | 0.0% | 0.0% | 0.1% | 0.2% |
| Globulins % of Protein Area | 64.6% | 0.0% | 0.0% | 64.1% | 64.5% |
| 2S + Pro-Napin % of protein Area | 35.4% | 0.0% | 0.0% | 35.9% | 35.5% |

C500 Sample, 1% W/V Lab #21,681

| Variable: | Reading: | Calculated Phenolics % on dry basis |
|---|---|---|
| Absorbance: 330-nm | 3.70 AU | 0.81% |
| pH | 5.83 | — | n.d. = not done, UF = ultrafiltered, DF = diafiltered, FD = freeze-dried, AU = Absorbance Units Globulins =>12S + 12S + 7S + sub-unit

TABLE 2

C500 Sample, BW-AL022-I02-03A #1 SD, Lab #20,576, Dec. 19, 2003

| Variable: | Sep. 8 Average | Std. Dev. | Dec. 17 Average | Std. Dev. |
|---|---|---|---|---|
| Moisture | 2.49% | 0.06% | n.d. | n.d. |
| Leco protein (as is) | 93.08% | 0.24% | 94.57% | 0.50% |
| Leco protein (dry basis) | 95.46% | 0.24%. | ad. | ad. |

C500 Sample, Lab #20,576, HPLC-SEC Results

| Variable: | C500 Sep. 8 Initial Test 1% W/V | C500 Dec. 17 Final Test 1% W/V |
|---|---|---|
| Protein % of Total Area | 72.5% | 73.0% |
| Phytate % of Total Area | 3.2% | 5.0% |
| Phenolics % of Total Area | 37.6% | 52.2% |
| Ascorbate % of Total Area | 4.6% | 0.7% |
| Misc. % of Total Area | 3.5% | 3.9% |
| >12S + 12S % of protein Area | 5.5% | 5.3% |
| 7S % of protein Area | 64.1% | 62.7% |
| 7S Sub-unit % of protein Area | 0.1% | 1.4% |
| Globulins % of Protein Area | 69.7% | 69.3% |
| 2S + Pro-Napin % of protein Area | 30.3% | 30.7% |

C500 Sample, 1% W/V Lab #20,576

| Variable: | Reading: | Calculated Phenolics % on dry basis |
|---|---|---|
| Absorbance: 330-nm | 1.45 AU | 0.32% |
| PH | — | — | n.d. = not done, UF = ultrafiltered, DF = diafiltered, SD = spray-dried, AU = Absorbance Units Globulins =>12S + 12S + 7S + sub-unit

TABLE 3

External Lab Results for BW-AL022-I02-03A
1 C500 Lab #20,576, Dec. 23, 2003

| Variable: | Sample as Received | Sample Dry Basis. |
|---|---|---|
| Moisture | 2.49% | — |
| Dry Matter | — | 96.07% |
| Crude Protein (Nx6.25) | 93.00% | 96.81% |
| Calcium | 0.10% | 0.10% |
| Phosphorus | 0.40% | 0.42% |
| Magnesium | 0.11% | 0.11% |
| Potassium | 0.31% | 0.32% |
| Copper | 0.0011% | 0.0011% |
| Sodium | 0.73% | 0.76% |
| Sodium Chloride equiv. | 1.85% | 1.92% |
| Zinc | 0.0007% | 0.0007% |
| Manganese | <0.0001% | <0.0001% |
| Iron | 0.0119% | 0.0124% |
| Boron | 0.0005% | 0.0005% |
| Lead[2] | 0.00 ppm | 0.00 ppm |
| Cadmium[2] | 0.00 ppm | 0.00 ppm |
| Mineral Sum[1] | 2.78% | 2.92% |

[1]Includes estimate of chloride for sodium.
[2]Both lead and cadmium are below threshold limits.

TABLE 4A

Burcon NutraScience Canola Retentate Amino Acid Summary

Analysis: POS Results: Jan. 5, 2004    g/100 g dry matter

| Amino Acid MW | Amino Acid | BW-AL022-I02-03A #1 #20,576 | Dec. 15, 2003 Bench #21,681 | Average | Std. Dev. |
|---|---|---|---|---|---|
| 133.1 | Aspartic | 7.04 | 7.46 | 7.25 | 0.30 |
| 119.1 | Threonine | 2.87 | 2.82 | 2.85 | 0.04 |
| 105.1 | Serine | 3.31 | 3.48 | 3.40 | 0.12 |
| 204.2 | Tryptophan | 1.28 | 1.38 | 1.33 | 0.07 |
| 146.1 | Glutamic | 20.10 | 21.70 | 20.90 | 1.13 |
| 75.1 | Glycine | 4.59 | 4.92 | 4.76 | 0.23 |
| 89.1 | Alanine | 3.75 | 4.02 | 3.89 | 0.19 |
| 121.1 | Cystine | 2.03 | 2.47 | 2.25 | 0.31 |
| 117.1 | Valine | 4.90 | 5.15 | 5.03 | 0.18 |
| 149.2 | Methionine | 1.57 | 1.84 | 1.71 | 0.19 |
| 131.2 | Isoleucine | 3.67 | 4.04 | 3.86 | 0.26 |
| 131.2 | Leucine | 6.66 | 7.37 | 7.02 | 0.50 |
| 181.2 | Tyrosine | 2.11 | 2.07 | 2.09 | 0.03 |
| 165.2 | Phenylalanine | 3.63 | 4.01 | 3.82 | 0.27 |
| 155.2 | Histidine | 2.07 | 2.08 | 2.08 | 0.01 |
| 146.2 | Lysine | 3.97 | 4.67 | 4.32 | 0.49 |
| 174.2 | Arginine | 6.45 | 6.77 | 6.61 | 0.23 |
| 115.1 | Proline | 6.56 | 6.83 | 6.70 | 0.19 |
|  | Sum: | 86.56 | 93.08 | 89.82 | on dry weight basis (DWB) |

Note that the two samples are protein isolates, based on crude protein (N × 6.25) and not on amino acid analyses.
Amino acid analyses usually results in loss of some nitrogen through deamination of glutamine and asparagine.

TABLE 4B

Amino Acid Summary: g/100 g Amino Acids

| Amino Acid MW | Amino Acid | BW-AL022-I02-03A #1 #20,576 | Dec. 15, 2003 Bench #21,681 | Average | Std. Dev. | Previous amino acid tests: Puratein LT A10 | Retentate A8 | Retentate A10-04 | |
|---|---|---|---|---|---|---|---|---|---|
| 133.1 | Aspartic * | 8.1 | 8.0 | 8.1 | 0.1 | 7.0 | 7.6 | 7.1 | Aspartic * |
| 119.1 | Threonine [e] | 3.3 | 3.0 | 3.2 | 0.2 | 3.8 | 3.8 | 3.8 | Threonine [e] |
| 105.1 | Serine | 3.8 | 3.7 | 3.8 | 0.1 | 3.9 | 3.9 | 4.0 | Serine |
| 204.2 | Tryptophan [e] | 1.5 | 1.5 | 1.5 | 0.0 | 1.4 | 1.2 | 1.5 | Tryptophan [e] |
| 146.1 | Glutamic * | 23.2 | 23.3 | 23.3 | 0.1 | 22.5 | 22.8 | 20.9 | Glutamic * |
| 75.1 | Glycine | 5.3 | 5.3 | 5.3 | 0.0 | 5.1 | 5.2 | 5.3 | Glycine |
| 89.1 | Alanine | 4.3 | 4.3 | 4.3 | 0.0 | 4.5 | 4.5 | 4.6 | Alanine |
| 121.1 | Cystine [e] | 2.3 | 2.7 | 2.5 | 0.2 | 2.7 | 2.2 | 2.9 | Cystine [e] |
| 117.1 | Valine [e] | 5.7 | 5.5 | 5.6 | 0.1 | 5.6 | 5.7 | 5.7 | Valine [e] |
| 149.2 | Methionine [e] | 1.8 | 2.0 | 1.9 | 0.1 | 2.1 | 1.9 | 1.9 | Methionine [e] |
| 131.2 | Isoleucine [e] | 4.2 | 4.3 | 4.3 | 0.1 | 4.4 | 4.5 | 4.5 | Isoleucine [e] |
| 131.2 | Leucine [e] | 7.7 | 7.9 | 7.8 | 0.2 | 7.8 | 7.9 | 8.0 | Leucine [e] |
| 181.2 | Tyrosine | 2.4 | 2.2 | 2.3 | 0.2 | 2.3 | 2.4 | 2.3 | Tyrosine |
| 165.2 | Phenylalanine [e] | 4.2 | 4.3 | 4.3 | 0.1 | 4.1 | 4.2 | 4.2 | Phenylalanine [e] |
| 155.2 | Histidine [e] | 2.4 | 2.2 | 2.3 | 0.1 | 3.2 | 2.7 | 3.3 | Histidine [e] |
| 146.2 | Lysine [e] | 4.6 | 5.0 | 4.8 | 0.3 | 5.3 | 4.9 | 5.5 | Lysine [e] |

TABLE 4B-continued

Amino Acid Summary: g/100 g Amino Acids

| Amino Acid MW | Amino Acid | BW-AL022-I02-03A #1 #20,576 | Dec. 15, 2003 Bench #21,681 | Average | Std. Dev. | Previous amino acid tests: Puratein LT A10 | Retentate A8 | Retentate A10-04 | |
|---|---|---|---|---|---|---|---|---|---|
| 174.2 | Arginine [e] | 7.5 | 7.3 | 7.4 | 0.1 | 7.1 | 7.4 | 7.2 | Arginine [e] |
| 115.1 | Proline | 7.6 | 7.3 | 7.5 | 0.2 | 7.3 | 7.0 | 7.4 | Proline |
| | Sum: | 100.0 | 100.0 | 100.0 | | 100.1 | 99.8 | 100.1 | |
| | Sum essential aa: | 45.2 | 45.8 | 45.5 | | 47.5 | 46.4 | 48.5 | |

[e] = 11 essential amino acids
aa = amino acids
\* Glutamic acid and aspartic acid are mostly deaminated glutamine and asparagine.

TABLE 5

Amino Acid Summary: g/100 g Amino Acids

| Amino Acid | AL022-I02-03A #1 #20,576 | Dec. 15, 2003 Bench #21,681 | Average | Previous Amino Acid Tests Puratein LT A10 | Retentate A8 | Retentate A10-04 | C200 A10 | C300 A10 |
|---|---|---|---|---|---|---|---|---|
| Aspartic * | 8.1 | 8.0 | 8.1 | 7.0 | 7.6 | 7.1 | 5.4 | 10.0 |
| Threonine [e] | 3.3 | 3.0 | 3.2 | 3.8 | 3.8 | 3.8 | 3.7 | 4.1 |
| Serine | 3.8 | 3.7 | 3.8 | 3.9 | 3.9 | 4.0 | 3.8 | 4.2 |
| Tryptophan [e] | 1.5 | 1.5 | 1.5 | 1.4 | 1.2 | 1.5 | 1.4 | 1.6 |
| Glutamic * | 23.2 | 23.3 | 23.3 | 22.5 | 22.8 | 20.9 | 22.8 | 19.0 |
| Glycine | 5.3 | 5.3 | 5.3 | 5.1 | 5.2 | 5.3 | 4.9 | 5.6 |
| Alanine | 4.3 | 4.3 | 4.3 | 4.5 | 4.5 | 4.6 | 4.7 | 4.7 |
| Cystine [e] | 2.3 | 2.7 | 2.5 | 2.7 | 2.2 | 2.9 | 3.4 | 1.2 |
| Valine [e] | 5.7 | 5.5 | 5.6 | 5.6 | 5.7 | 5.7 | 5.4 | 6.1 |
| Methionine [e] | 1.8 | 2.0 | 1.9 | 2.1 | 1.9 | 1.9 | 2.1 | 1.6 |
| Isoleucine [e] | 4.2 | 4.3 | 4.3 | 4.4 | 4.5 | 4.5 | 4.2 | 5.0 |
| Leucine [e] | 7.7 | 7.9 | 7.8 | 7.8 | 7.9 | 8.0 | 7.6 | 8.6 |
| Tyrosine | 2.4 | 2.2 | 2.3 | 2.3 | 2.4 | 2.3 | 2.0 | 2.8 |
| Phenylalanine [e] | 4.2 | 4.3 | 4.3 | 4.1 | 4.2 | 4.2 | 3.8 | 4.9 |
| Histidine [e] | 2.4 | 2.2 | 2.3 | 3.2 | 2.7 | 3.3 | 3.6 | 2.6 |
| Lysine [e] | 4.6 | 5.0 | 4.8 | 5.3 | 4.9 | 5.5 | 6.4 | 3.6 |
| Arginine [e] | 7.5 | 7.3 | 7.4 | 7.1 | 7.4 | 7.2 | 6.7 | 7.8 |
| Proline | 7.6 | 7.3 | 7.5 | 7.3 | 7.0 | 7.4 | 8.2 | 6.7 |
| Sum: | 100.00 | 100.00 | 100.00 | 100.1 | 99.8 | 100.1 | 100.1 | 100.1 |

Puratein is blend of C200 and C300, close to the expected composition of C500.
Current analyses slightly on low side for threonine and histidine and slightly higher for glutamic acid.
Overall, analyses are very similar and lie between typical analyses for C200 and C300, as expected.

TABLE 6

Amino Acid Requirements of Teleost vs Burcon Retentates in g/100 g protein

| Amino Acid | Salmonid[1] | Catfish[1] | Carp[1] | BW-AL022-I02-03A #1 | Dec. 15, 2003 Bench Trial |
|---|---|---|---|---|---|
| Arginine | 4.2 | 4.3 | 4.4 | 7.5 | 7.3 |
| Histidine | 1.6 | 1.5 | 2.4 | 2.4 | 2.2 |
| Isoleucine | 2.0 | 2.6 | 3.0 | 4.2 | 4.3 |
| Leucine | 3.6 | 3.5 | 4.7 | 7.7 | 7.9 |
| Lysine | 4.8 | 5.0 | 6.0 | 4.6 | 5.0 |
| Threonine | 2.0 | 2.1 | 4.2 | 3.3 | 3.0 |
| Tryptophan | 0.6 | 0.5 | 0.8 | 5.7 | 5.5 |
| Valine | 2.2 | 3.0 | 4.1 | 5.7 | 5.5 |
| Methionine + Cysteine | 2.4 | 2.3 | 3.5 | 4.1 | 4.7 |
| Phenylalanine + Tyrosine | 5.3 | 4.8 | 8.2 | 6.6 | 6.5 |

[1] D. P. Bureau & C. Y. Cho, Fish Nutrition Research Laboratory, Dept. of Animal & Poultry Science, University of Guelph, Guelph, Ontario, Canada

What we claim is:

1. A feed composition for aquaculture comprising a canola protein isolate having a protein content of at least about 90 wt % (N×6.25) on a dry weight basis and having a canola protein profile which is about 40 to about 50 wt % of 2S canola protein, about 50 to about 60 wt % of 7S canola protein and about 1 to about 5 wt % of 12S canola protein.

2. The feed composition of claim 1 wherein said canola protein isolate has a protein content of at least about 100 wt % (N ×6.25).

* * * * *